United States Patent [19]
Revesz

[11] Patent Number: 5,378,878
[45] Date of Patent: * Jan. 3, 1995

[54] HEAT RESISTANT AND LIGHT WEIGHT CONTAINER FOR MATERIALS TO BE HEATED, AND PROCESS FOR MANUFACTURE THEREOF

[75] Inventor: Robert N. Revesz, Monroe, N.C.

[73] Assignee: CEM Corporation, Matthews, N.C.

[ * ] Notice: The portion of the term of this patent subsequent to Nov. 19, 2008 has been disclaimed.

[21] Appl. No.: 663,441

[22] Filed: Mar. 1, 1991

Related U.S. Application Data

[63] Continuation-in-part of Ser. No. 298,553, Jan. 18, 1989, Pat. No. 5,066,843.

[51] Int. Cl.⁶ ............................................. H05B 6/80
[52] U.S. Cl. .................................. 219/762; 219/679; 264/26; 432/258; 422/78; 436/155
[58] Field of Search ............... 219/10.55 R, 10.55 F, 219/10.55 E, 10.55 M, 762, 679, 725, 728, 730, 759, 678; 126/390; 264/25, 26, 345, 346, DIG. 46; 422/78, 21; 436/155; 432/258

[56] References Cited
U.S. PATENT DOCUMENTS

| | | | |
|---|---|---|---|
| 3,645,703 | 2/1972 | Frank et al. | 29/182.5 |
| 3,731,037 | 5/1973 | Levinson | 219/10.55 E |
| 3,773,669 | 11/1973 | Yamauchi et al. | 219/10.55 E |
| 4,003,368 | 1/1977 | Maxel | 219/10.55 E |
| 4,495,775 | 1/1985 | Young et al. | 206/0.7 |
| 4,565,669 | 1/1986 | Collins et al. | 422/78 |
| 4,773,952 | 9/1988 | Wesley, Jr. | 220/414 |
| 5,066,843 | 11/1991 | Revesz | 219/10.55 R |

Primary Examiner—Philip H. Leung
Attorney, Agent, or Firm—Raymond F. Kramer

[57] ABSTRACT

A highly preferred container for ashable material, which material is to be ashed by heat in an ashing furnace, while it is in such container, especially when such container is to be heated by microwave radiation onto microwave absorptive elements of the furnace, which thereby heat the container, is a heat resistant, walled container which is light weight, microwave transmissive, porous and air transmissive, which is of quartz microfibers that are held in desired walled container form, preferably in substantially flat cylindrical form. Such a container may be made by shaping a heat resistant, light weight, microwave transmissive and porous non-woven sheet of quartz microfibers to container form and heating and curing such sheet in such form, preferably after moistening it with water, whereby a form-retaining container results that can be successfully employed to hold ashable samples to be ashed for analysis during microwave powered ashings of such samples. The described containers may also be made by formation directly from the quartz microfibers, followed by sintering thereof to a form retaining article. Although pure quartz microfibers are preferred for the described containers they may contain or may be made of borosilicate glass, in which case their microwave transmission and high temperature stability can be decreased.

19 Claims, 3 Drawing Sheets

HEAT RESISTANT AND LIGHT WEIGHT CONTAINER FOR MATERIALS TO BE HEATED, AND PROCESS FOR MANUFACTURE THEREOF

This application is a continuation-in-part of my application Ser. No. 07/298,553, filed on Jan. 18, 1989, which issued as U.S. Pat. No. 5,066,843 on Nov. 19, 1991.

The present invention, like that of Ser. No. 07/298,553, relates to a container which is suitable for holding an ashable material to be ashed in a high temperature ashing furnace. More particularly, it relates to such a container which is heat resistant, light in weight, microwave transmissive and porous, and which is made of quartz microfibers which are held together in walled container form. However, the ashing containers of the present invention may be of other sizes and physical characteristics (they may be better) than those specifically recited in Ser. No. 07/298,553.

Prior to the invention of Ser. No. 07/298,553 quartz fiber discs had been disclosed as supports for samples to be ashed by heat generated by directing microwave energy onto microwave absorptive materials. In U.S. Pat. No. 4,565,669, issued to Collins and Hargett, a quartz fiber support pad and a cover of the same material were utilized to confine an ashable analytic sample, to be analyzed, during the ashing of such sample by heat generated by directing microwave radiation at microwave absorptive silicon carbide under such a support pad. U.S. Pat. No. 4,565,669 represents the closest art known to applicant prior to the filing of Ser. No. 07/298,553 but it does not describe or suggest the subject matter of the present invention and does not make it obvious, and the ashing process of the patent does not result in the improved ashing that is obtainable with the invented container.

In accordance with this invention a container for a material which is to be heated therein, which container is microwave transmissive and heat resistant during such heating operation, light in weight and porous, and includes integral bottom and side wall portions made of quartz fibers, borosilicate glass fibers or a mixture of quartz fibers and borosilicate glass fibers, which bottom and side wall portions are held together in integral walled and bottomed container form. Also within the invention is a process for manufacturing such a container by shaping of a light weight, microwave transmissive and porous sheet of such microfibers or a plurality of such sheets to container form and heating such sheet or plurality of such sheets in such form, preferably after wetting and drying it or them, whereby a form retaining container results, which is resistant to ashing temperatures and other ashing conditions. The containers of this invention can also be made by the process described in Ser. No. 07/662,915, abandoned of the present inventor and his coinventor, James E. Thomas, entitled Process for Manufacture of Ashing Containers, or they can be made by modifications of such process and of others herein described.

Although the invented containers are very preferably of quartz microfibers such microfibers way also be made of borosilicate glass or of mixed borosilicate glass and quartz microfibers, in which case microwave transmission and heat stability will be decreased. In view of the feasibility of using borosilicate glass in place of some or all of the quartz it should be understood that in this specification when quartz is mentioned as being employed borosilicate glass can be substituted, especially for lower temperature and non-microwave ashings, although quartz is much preferred.

The invented containers are especially useful in conjunction with microwave ashing apparatuses like that described in an application for patent, Ser. No. 07/298,554, of Michael J. Collins and Wyatt P. Hargett, entitled Microwave Ashing and Analytical Apparatuses, Components and Processes, which was filed on Jan. 18, 1989. The disclosures of such application, Ser. No. 07/298,553 and the co-filed application are hereby incorporated herein by reference, together with the disclosure of U.S. Pat. No. 4,565,669. However, the invented containers also find use in other ashing applications, such as those conducted in conventional muffle furnaces, and in other heating operations, including fusions and dry ashings (wherein ash is produced for subsequent analyses, such as for heavy metals).

The invention will be readily understood by reference to this specification, including the accompanying drawing, in which.

Figure 1:
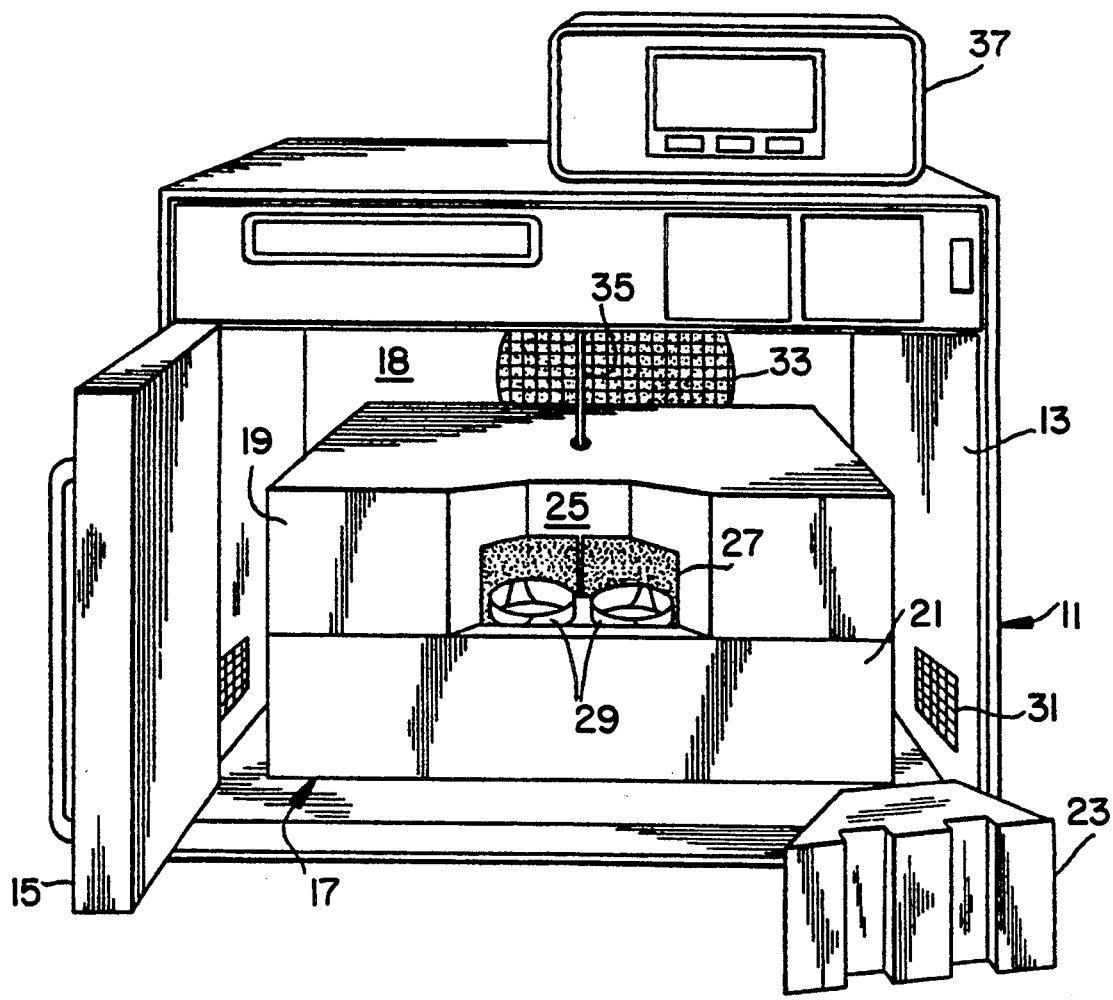
FIG. 1 is a front perspective view of a microwave ashing apparatus, with chamber door open and with furnace door removed to illustrate two of the invented containers in the furnace.

In FIG. 1 a microwave ashing apparatus 11 comprises top, bottom, side and rear walls, all designated by numeral 13, applied to a side wall, and door 15, which define a microwave retaining chamber 18. Inside the chamber is a furnace 17, which includes top and bottom portions 19 and 21, and a furnace door 23. Such furnace parts are made of microwave transmissive open celled quartz, which is of low thermal conductivity and is heat resistant, capable of being employed at very high temperatures without deterioration. Such a type material is ECCOFOAM® Q, preferably ECCOFOAM Q-G, which is described in a bulletin entitled ECCOFOAM Plastic and Ceramic Foams, of Emerson and Cumming, Canton, Massachusetts, dated March, 1980, hereby incorporated herein by reference. Inside the furnace is a furnace cavity 25 and microwave absorptive material 27 is located in grooves or slots (not shown) in the upper and lower portions 19 and 21, with surfaces thereof even with the internal surfaces that define the furnace cavity. In the furnace cavity are illustrated two of the containers of the present invention, which are designated by numeral 29. Also shown in FIG. 1 are inlets 31 for air to enter the chamber, part of which air will pass through the furnace cavity, but most of which passes around the chamber 18 and serves to cool the walls thereof. Such air exits the chamber through outlet 33. A thermocouple 35 is located in the furnace cavity and is communicated by means of a connector (not illustrated) to temperature controller 37. Both the main microwave generating unit of apparatus 11 and temperature controller 37 include controls and visual displays, which are readily apparent and therefore are not specifically numbered.

Figure 2:
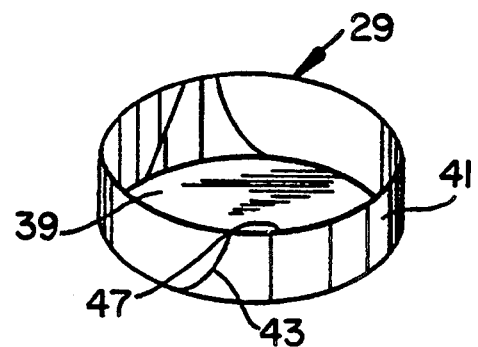
FIG. 2 is a top front perspective view of a walled ashing container of the present invention.

In FIG. 2 there is illustrated one of the containers of the present invention. Such container is of unitary construction, with bottom 39 and side wall 41 being made from the same sheet of porous unwoven quartz microfibers. The container illustrated had been made from a square portion of the fibrous material and includes seam lines like that shown at 43.

Figure 3:
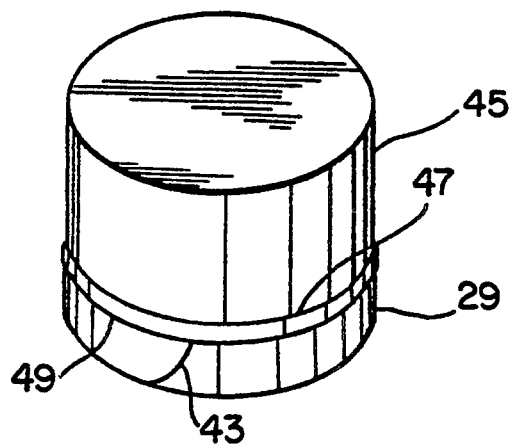
FIG. 3 is a top front perspective view of an ashing container of the present invention having the side wall thereof being formed about a mandrel from a sheet of nonwoven fibrous quartz.

In FIG. 3 there is illustrated a step in the manufacture of container 29. As shown, the non-woven microfibrous quartz sheet has been formed about the base of cylindrical mandrel 45 and extra material has been trimmed off along top edge 47. A quartz monofilament 49 or an elastic band or similar restraining means holds the porous microfibrous quartz sheet tightly to the mandrel during the forming operation but is later removed, following normal manufacturing procedure. After shaping of the sheet, it is wetted, formed tightly around the mandrel, trimmed, removed from the mandrel and air dried, after which it is heated (fired) to produce the form-retaining container of this invention. While air drying is preferred it may sometimes be omitted. Also heating (which may involve partial fusing or sintering) may be effected while the container is on the mandrel if the mandrel material is heat resistant.

Figure 4:
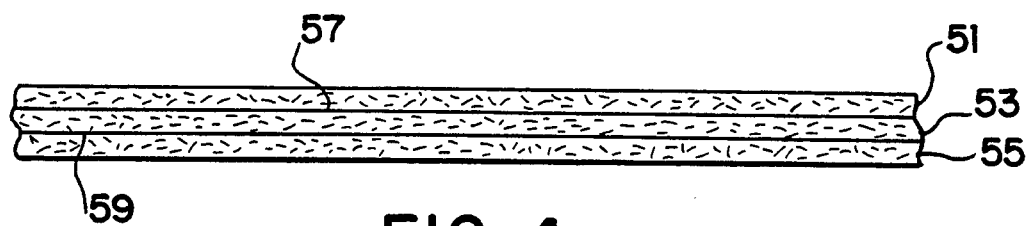
FIG. 4 is a side view of a plurality of sheets of nonwoven microfibrous quartz, from which a container of greater wall thickness than that of FIG. 2 can be made.

In FIG. 4 there are shown three microfibrous quartz sheets (or portions thereof) 51, 53 and 55, with major surfaces thereof in contact with one another along planes 57 and 59. Such sheets may be laminated together or may be in relatively loose contact, and may be formed into a-thicker walled container (thicker than that obtained by the forming of such a container from a single sheet) when that may be desired. Such a thicker container may be from 2 to 5, or even more, times the thickness of a container made from a single sheet of non-woven quartz microfibers. Further variations in container thicknesses (and porosity and permeability to air flow) are obtainable by utilizing microfibrous sheets of different initial thicknesses, as single sheets, multiple sheets or laminates.

Figure 5:
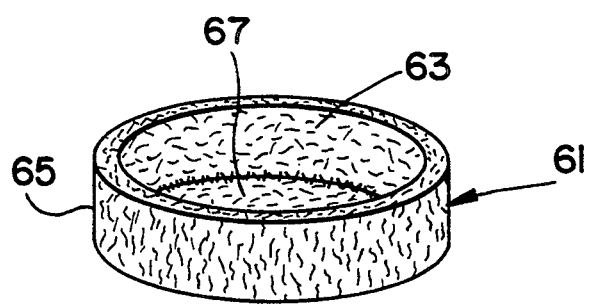
FIG. 5 is a perspective view of a container of this invention that is made by the process of the co-filed Revesz-Thomas application entitled Process for Manufacture of Ashing Containers.

In FIG. 5 there is shown an ashing container 61 of this invention which was made by the process described in the co-filed Revesz-Thomas application entitled *Process for Manufacture of Ashing Containers*. Container 61 may be of essentially the same dimensions as the previously referred to containers and will be of similar physical properties but will often be of increased air permeability, which is often desirable. Container 61 is made up of quartz microfibers 63 that are formed into integral side wall 65 and bottom 67 portions by deposition of the fibers from a slurry of such fibers in a liquid medium onto a form which is liquid transmissive, after which the article is removed from the form, dried and "fired" or sintered to form-retaining integral containers. Integral wall 65 and bottom 67 portions of the container are of substantially the same thickness, strength and air permeability but they may be of different such characteristics, too.

Although the invented container is illustrated as a short cylinder, other container shapes may also be produced, utilizing correspondingly shaped mandrels or forms. Thus, containers of rectangular or square horizontal cross-sections may be produced. Although various shapes of containers may be made it will be preferred that such containers be relatively flat, usually being of a height/major horizontal dimension ratio less than 1:1 and preferably not more than 1:2. Such preferred ratios, as for height/diameter, may be in the range of 1:2 to 1:10, preferably being in the range of 1:2 to 1:5, e.g., about 1:3. While various sizes of containers may be employed, when such containers are flat and cylindrical it will normally be preferred for them to be from 2 to 10 cm. in diameter, preferably 4 to 6 cm., and 0.5 to 4 cm. high, preferably 1 to 2 cm. high, e.g., about 4.7 cm. in diameter by about 1.5 cm. in height (all dimensions being outside measurements).

The unitary container made is heat resistant (high temperature stable), light in weight, microwave transmissive and porous, and is made of quartz microfibers which are held together in walled container form. The quartz microfibers are of generally circular cross-sections, often being sub-micron or micron sized, such as in the range of 0.2 to 7 microns or 0.3 to 2 microns, on the average, e.g., about 0.6 or 0.7 microns, with lengths that may average or be in the range of 10 to 1,000 or so times such diameter. Such microfibers, when present in thin sheet or sheet-like form, preferably being non-woven, are heat shaped, "fired" or sintered to form-retaining container shape. The microfibrous quartz sheet plurality of sheets or a container wall will be of a thickness in the range of 0.2 to 5 mm., preferably 0.3 to 4 mm., e.g., 2 or 3 mm., and preferably will be of porosity so that the pressure drop across it is such as not to unduly impede air flow through the container wall during ashing operations, often being in the range of 0 to 10 mm. of mercury at about 1 cm./sec. face velocity of air (but it may even be in such range at higher velocities, even up to 30 or 40 cm./sec.), e.g., 4 mm. of Hg at 5 cm./sec., resistant to high temperatures, such as 400° C., 500° C. or even 1000° C. without significant adverse effects, retentive of micron size particles, transmissive of microwave radiation, and of a weight in the range of 50 to 500 g./sq. m. or a density in the range of 0.02 to 0.25 g./cc. And more preferably the material will be of a thickness in the range of 0.3 to 3 mm. or 4 mm., of such porosity that the pressure drop is 0 to 8 or 0 to 6 mm. of mercury, heat stable, even up to 950° or 1,000° C. (although some embrittlement may occur), retentive of over 99% of micron size particles, transparent to applied heating microwave radiation, and of a weight in the range of 50 to 250 g./sq. m. or a density in the range of 0.02 to 0.13 g./c. cm. Ideally the pressure drop across the porous wall and bottom portions will be in the range of 0 to 1 or 2 mm. of mercury, to maximize gas transmissions. Such a container will normally weigh in the range of 0.2 or 0.3 to 2 g., preferably weighing in the range of 0.3 to 0.8 g.

A very suitable material of construction for the present containers is that sold by Whatman Laboratory Products, Inc., Clifton, N.J., for use as air pollution filters, under the name Whatman ® Ultra-Pure QM-A Quartz Filters, which are described in their publication No. 860-QM-AA (2 pages), which is hereby incorporated herein by reference. According to such publication, the described material is an ultra-pure quartz microfiber filter sheet which contains a small proportion (5%) of conventional borosilicate glass microfibers, which are in the sheet for papermaking purposes. Such publication does not describe or suggest the use of the mentioned material as a container, does not refer to ashing of analytical samples, and does not mention the use of microwave heating for ashing such samples or for heating or ashing other materials. According to the Whatman publication the weight of the QM-A quartz filter is 85 g./m.$^2$, its thickness is 0.45 mm., it retains 99.999% of 0.6 micron particles at 5 cm./sec. face velocity of air, it is of a dry tensile strength, for a 1.5 cm. wide strip, of 250 to 300 g., and it is capable of withstanding a maximum temperature of 500° C. Also according to such data sheets the material contains 0.2 p.p.m. of cadmium, 1.1 p.p.m. of cobalt, 1.6 p.p.m. of chromium, 3.4 p.p.m. of copper, 23.0 p.p.m. of iron, 0.5 p.p.m. of manganese, 3.4 p.p.m. of nickel, 2.3 p.p.m. of lead and 18.2 p.p.m. of zinc, which analysis qualifies it as an ultra-pure filter material.

To make the present containers, of the type illustrated in FIGS. 1-4, a relatively simple process is employed, in which a non-woven sheet (or a plurality of such sheets, contiguous on major surfaces thereof, as in FIG. 4) of the described microfibrous quartz is shaped on a mandrel, wetted, formed, trimmed, removed from the mandrel, air or vacuum dried and fired. If restraint and mandrel materials are sufficiently heat resistant the firing may be conducted while the sheet material is held in place on the mandrel. Such heating is to a sufficiently high temperature to result in a form-retaining container, which temperature will normally be at least 400° C. but is preferably in the range of 500° to 1,200° C. Heating time at the desired "curing" temperature will normally be in the range of 1 to 20 minutes, with ranges of 1 to 15 minutes and 5 to 12 minutes being preferred and more preferred. For example, a 10 minute heating period at about 800°-1,000° C. is often employed. It has been theorized that during the curing operation any borosilicate glass which may be present as a component of the microporous quartz filter material is removed, leaving a formed container of quartz fibers which are still porous and which are even more heat resistant than the starting material. However, applicant is not bound by such theory.

The described heating or firing of the container may be effected in various heating means, including ovens and muffle furnaces, but preferably is conducted in a microwave ashing furnace of the type in which the container is primarily intended to be employed. Preferably the heating will be to a temperature at least as high as that to which the container will be subjected during ashing operations, but lower temperatures can also suffice. Moistening of the sheet material may be effected before shaping, as well as after, and such moistening may be by spraying, roll application or immersion. It will usually be preferable to limit the amount of moisture on the microporous quartz material being shaped to that amount which is effective to facilitate its shaping to desired container form, which amount will usually be that which is sufficient to wet all such material. Drying before firing may be conducted on or off the mandrel, and may be by hot air, radiant heating or other means, in addition to ambient air drying.

When a mandrel or other form for the microporous sheet is not used during firing to form retaining configuration, as when a flaring dish shape is desired, the sheet may be formed to such a shape and during heating the outer edges thereof may be unsupported or may be supported, as by the upper walls of a larger cylinder. Various types of forms may be employed, including sleeves between which the desired container walls are held during heating, but for the manufacture of the preferred relatively short cylindrical containers a corresponding cylindrical mandrel, like that illustrated in FIG. 3, will preferably be utilized. Such mandrel may be of any suitable material, including various glasses, plastics, metals and alloys, such as copper, brass, steel and stainless steel, but if the mandrel is to be in place during firing it should also be heat resistant. If the heating of the shaped sheet on the form is to be carried out in a microwave ashing apparatus, in which the presence of metals will often be avoided, the form is desirably of a microwave transparent material, such as quartz, although various ceramics and glasses may also be employed under proper circumstances. Whichever firing procedure is followed, it will be satisfactory, providing that the container wall does not collapse or distort objectionably.

The heating or firing is preferably undertaken in a microwave ashing apparatus like that described in previously mentioned co-pending patent application Ser. No. 07/298,554. Utilization of such apparatus is convenient and puts the containers made to a test which almost duplicates actual use conditions. Heating in such apparatus will normally be to the range of about 800° to 1,000° C., e.g., 850°, 950° or 1,000° C., but may be in the previously mentioned range of 500° to 1,200° C. and can even be as low as 400° C. or as high as 1,600° C. under some circumstances.

It will be noted that in the foregoing recitation of sintering temperatures many are in excess of the maximum temperature listed by the manufacturer of the quartz fiber sheets, which is 500° C. Surprisingly, applicant has found that his containers can be made to be shape-retentive by heating to temperatures close to or in excess of the temperature given by the manufacturer as the maximum temperature to which the manufacturer's filter materials should be raised during use. During such heating operation the formerly flat sheet or filter material is converted to a form-retaining container, useful to hold ashable samples for microwave ashing operations. Such permanent shaping of the sheet material takes place at temperatures below the melting point of quartz and the porous sheet does not lose its porosity due to the sintering or partial fusions effected. It appears that the presence of the small proportion (1 to 10%) of borosilicate glass micro-fibers in the quartz sheet is helpful in manufacturing the present containers but such is not considered to be essential for obtaining the desired result. It is considered that other glasses may be substituted for the borosilicate glass, or that such glasses may be omitted, and still, useful form-retaining containers for microwave ash analyses may be made.

After heating is completed the container will be removed from the source of heat and will be allowed to cool in air to room temperature. Slow cooling is favored to relieve strains and to avoid excessive embrittlement. Cooling times (to room temperature) from 30 seconds to ten minutes are considered to be useful to produce satisfactory microwave ashing containers.

In use, a container of the present invention, singly or with other such containers, and sometimes with an insert of similar material, is weighed, has ashable sample added to it, after which it is again weighed, has a solution of dispersing agent, such as ethanol solution of magnesium acetate, applied to the ashable specimen, while in the container (when flour is being analyzed), and then the sample is ashed in a microwave ashing apparatus, such as that illustrated in FIG. 1, which apparatus is described in more detail in co-pending Ser. No. 07/298,554. After completion of ashing the container of ash, with the ash on magnesium oxide (the "ash" from the magnesium acetate), is weighed and the amount of ash and the percentage thereof in the original analytical sample are calculated (such can be done because the weight of the magnesium oxide is known from the amount of magnesium acetate solution employed).

Although the ashing temperature in the microwave ashing apparatus may be in excess of the 500° C. maximum temperature specified by the filter manufacturer, it has been found that the invented container can be satisfactorily employed in high temperature ashings without deterioration sufficient to affect adversely the accuracy of the ash content determination. In fact, the same container can be used for a plurality of microwave ashing analyses, often more than 5 and up to 50, e.g., 10. With continued use the container may become more brittle but if handled carefully it will be employable in the numbers of analyses mentioned without losing desired porosity for such ashing, without breaking and without leaking sample or ash.

In addition to the unexpected advantage of high temperature utility the containers of the present invention possess several other unexpected advantages and characteristics that make them ideal for microwave ashing and microwave ashing analyses. The microfibrous quartz material employed is porous, and allows air to pass through it without resulting in loss of sample or ash. This is important because it promotes ignition and oxidation of the sample (most of the ash being in the form of oxides). When a dispersing agent, such as magnesium acetate in ethanol, is employed to treat the ashable sample before ashing, the porosity of the container material (which is maintained despite the higher temperature heating thereof in the forming operation), is contributory to smooth flaming of the solvent, rather than what resembles an explosive combustion of the solvent, which could carry away some of the sample. Such smooth flaming is believed to occur partly because the ethanol of the magnesium acetate solution spreads over the container due to the container's absorptive and/or adsorptive properties. The smooth flaming or combustion may also be partially attributable to the relatively low height of the container wall and the porosity and air transmissivity, both of which facilitate access of air to the sample and to the ethanol present. With the present containers such flaming can be effected in the furnace of the microwave apparatus during the automated ashing operations whereas when ordinary non-porous crucibles of quartz, porcelain or platinum are employed in muffle furnaces or in microwave ashing furnaces, when suitable, it is usually desirable to remove the alcohol from the sample by flaming it externally of the furnace before beginning the ashing operation. The described advantages are also obtainable when the ashings are conducted in other types of furnaces, e.g., muffle furnaces.

In addition to being porous, the present containers are light in weight and are of low thermal conductivity. Because they are light in weight their weights are often significantly less than the sample weights and may even be less than the ash weights, in some instances, which leads to more accurate weighings of the sample and ash. Furthermore, despite low thermal conductivity the lightweight and porous container cools faster when removed from the ashing furnace, so time is saved in cooling the container and ash before weighing, compared to when an ordinary crucible is employed. The invented containers, often being thinner than ordinary crucibles and other containers, also more readily transfer heat to ashable samples from external heat sources, such as microwave absorptive heating elements and refractory muffle furnace walls.

Because the invented containers have side walls, they are superior to the flat support pads described in U.S. Pat. No. 4,565,669, and do not require cover pads to prevent loss of feathery ash into the exit air passing through the furnace and the ashing chamber of the microwave ashing apparatus. The wall has the desired effect of allowing access of oxidizing air to the sample while at the same time diminishing its velocity, so as to prevent any loss of ash from the container. However, as a safety measure, if it should be desired, a cover can be employed on the present containers, which may be made of the same material, shaped to suit, or may be of a more open porous material or screening, preferably of quartz filaments or fibers.

The following examples illustrate but do not limit the present invention. Unless otherwise indicated, all parts are by weight and all temperatures are in ° C.

EXAMPLE 1

A 9 cm. ×9 cm. square of Whatman Ultra-Pure QM-A quartz filter, which is a non-woven sheet of quartz microfibers, is shaped about a substantially cylindrical glass form to a flat cylinder with a base about 6 cm. in diameter, and then the cylinder is wetted with about 3.0 g. of water, which is applied by spraying it substantially evenly over the surfaces of the filter material. An elastic band is then applied to the cylinder wall, as illustrated in FIG. 3, to hold such wall in position. The application of water to the filter helps it to retain the desired cylindrical shape. Subsequently, the filter is trimmed and the elastic band is removed. Next the cylinder is removed and is air dried, and then it is heated (or fired) in a muffle furnace for about ten minutes at about 870° C. to cure it, after which it is removed from the muffle furnace and allowed to cool in room temperature air. The result is a form-retaining, sintered short cylindrical container, useful for microwave ashing of ashable materials, such as analytical specimens. The container looks like that of FIG. 2 and those of FIG. 1. Although the container is form-retaining, even during use at elevated temperatures as a container for ashable material during microwave ashing thereof, it retains its desirable porosity.

Alternatively, the container may be fired in a microwave ashing furnace like that illustrated in FIG. 1, at a higher temperature, 950° or 1,000° C., and the result is the same.

EXAMPLE 2

An ashing container in flat cylindrical form, essentially the same as that of Example 1 and FIG. 2, is made by wetting a 9 cm.×9 cm. square of the same QM-A filter material with the same amount of water, forming it by means of a quartz mandrel, as shown in FIG. 3, into a flat cylinder, trimming such cylinder to desired 1.5 cm. height, and holding a side wall thereof to the mandrel by means of a quartz thread, also as illustrated in FIG. 3. The shaped cylinder, on the quartz mandrel, is then subjected to a curing heating to a temperature of 950° C. for ten minutes in a microwave furnace, like that of FIG. 1, after which the heating is discontinued and the mandrel and flat cylindrical container are removed from the microwave furnace and allowed to cool in room temperature air. After cooling, the container is removed from the mandrel and is ready for use, usually after removal of the quartz thread.

EXAMPLE 3

(Use of Invented Container in Microwave Ashing Apparatus)

The container described in Example 1, which weighs 0.50 g., has added to it 2.01 g. of a check sample of wheat flour (from the American Association of Cereal Chemists) and to the sample in the container there are applied approximately 3 ml. of a 15 g./l. ethanol (95%) solution of magnesium acetate, in such manner as to wet all the sample (and also to wet part of the container). The container of test sample, wetted with the magnesium acetate solution, is placed in the microwave ashing furnace of FIG. 1 (described in more detail in co-pending patent application Ser. No. 07/298,554) after such apparatus furnace is brought to a temperature of 935° C., and heating at such temperature is continued for ten minutes. Such heating is then halted and the container of ash is removed. The weight of flour ash and magnesium oxide is 0.02 g. and the weight of magnesium oxide (previously obtained experimentally for the volume of solution added) is 0.01 g. Thus, the cereal ash weighed 0.01 g., which corresponds to 0.05% of ash, which checks with results obtained by standard muffle furnace ashing (over a 90 minute period) and analysis of the same sample.

In variations of this experiment containers produced by the procedure described in Example 1 as alternative, by the procedure illustrated in Example 2, and by the procedure described in conjunction with the explanation of FIG. 5 are substituted and the results are essentially the same. Furthermore, when a plurality of samples is ashed at the same time, in a plurality of such containers in a microwave ashing apparatus, such as illustrated in FIG. 1, accurate results for each are also obtainable.

EXAMPLE 4

Containers within the invention that are made from a microfibrous quartz filter sheet material or quartz microfibers that do not contain borosilicate glass (which is present in the QM-A filter material) can also be made by the processes described, with suitable heating temperatures being employed in the range of 500° to 1,000° C., such as 950° C., and will be satisfactory, even when only half the water is applied and when no water is applied beforehand to the sheet material (other suitable liquids, such as ethanol, may also be substituted). Also, the described containers may be made by sintering together quartz microfibers that are formed into containers by deposition on a form, as described in the concurrently filed Revesz-Thomas patent application. Such containers are employable in microwave ashing apparatuses like those illustrated in FIG. 1 and in co-pending Ser. No. 07/298,554, and accurate analytical results are obtainable, as is verifiable by comparison with standard muffle furnace analyses of the same test samples.

In addition, ash analyses of other materials, including other grain flours, synthetic organic polymeric plastics such as polyethylene and polypropylene (analyzed for filler contents), coal (analyzed for ash content), oil (analyzed for trace elements contents), stream sediments, waste water sludges, milk powder and many other ashable materials, are successfully performable using the described procedures and apparatuses (except that in various of such analyses magnesium acetate needs not be employed). In such ashings the ashing temperature is varied within a 500° to 1,000° C. range and the ashing times are also varied, usually from 8 to 20 minutes, which will depend on the type of material being ashed and its ashing temperature. In all such instances satisfactory ashings and analyses are the results, which correspond with determinations made following standard muffle furnace procedures applied to the same test specimens. Such good results are also obtained when the cylindrical ashing container is covered by a flat cylindrical cover of the QM-A filter material, but use of such cover is not necessary.

In another variation of the invention instead of quartz microfibrous material or mixed quartz and borosilicate glass micro-fibrous material, borosilicate glass microfibrous material may be employed to make the subject containers, which may be used for lower temperature, e.g., 500° C., ashings in muffle furnaces with satisfactory results, although such containers are not suitable for higher temperature, e.g., 1,000° C., microwave furnace ashings. Also ordinary glass in microfiber form may be employed to make containers like those previously described but such will not have the microwave transmission or high temperature resistant characteristics of microfibrous quartz containers, so their uses will often be limited to heating and drying operations. If desired, the microfibrous quartz ashing containers may be used as such in muffle furnace ashings but for speedier but accurate analyses microwave ashing operations are preferable.

The invention has been described with respect to illustrations, working embodiments and descriptions thereof but is not to be limited to these because it is evident that one of skill in the art, with the present specification before him, will be able to utilize substitutes and equivalents without departing from the invention.

What is claimed is:

1. A container for a material which is to be heated therein, which container is microwave transmissive and heat resistant during such heating operation, light in weight and porous, and includes integral bottom and side wall portions made of quartz fibers, borosilicate glass fibers or a mixture of quartz fibers and borosilicate; glass fibers, which bottom and side wall portions are held together in integral walled and bottomed container form.

2. A container according to claim 1, which includes integral bottom and side wall portions which are thin walled and porous to air flow through them during ashings of ashable analytic samples, and which are of non-woven microfibers sintered together.

3. A container according to claim 2 wherein the material of construction thereof is a non-woven thin sheet of microfibers which are quartz microfibers, borosilicate glass microfibers or a mixture of quartz microfibers and borosilicate glass microfibers, which sheet has been sintered or partially fused to walled and bottomed container form.

4. A container according to claim 1, which is heat resistant during ashing operations and in which the fibers are microfibers.

5. A container according to claim 4 which is made of quartz fibers.

6. A container for a material which is to be heated therein, which container is heat resistant during such a heating operation, light in weight and of integral thin walled bottom and side wall portions which are porous to air flow through them during ashings of ashable analytical samples, which bottom and side wall portions are of non-woven microfibers which are quartz microfibers, borosilicate glass microfibers or a mixture of quartz microfibers and borosilicate glass microfibers, which non-woven microfibers are sintered together so as to be in integral walled and bottomed container form, wherein the container wall and bottom portions are resistant to a temperature of 500° C., are of a thickness in the range of 0.2 to 5 mm, are of a weight in the range of 50 to 500 g/m$^2$, are retentive of micron size particles and are of such a porosity that the pressure drop across them is in the range of 0 to 10 mm of mercury at a face velocity of air in the range of 1 to 10 cm per second.

7. A container according to claim 6 wherein the material of construction is of quartz microfibers and is of a thickness in the range of 0.3 to 4 mm, of such porosity that the pressure drop across it is in the range of 0 to 6 mm of mercury at about 1 cm/second face velocity of air, heat resistant, with some embrittlement, to about 1,000° C., retentive of over 99% of micron size particles and transparent to microwave radiation.

8. A container according to claim 7 which is of substantially flat cylindrical form, with the height/diameter ratio thereof being in the range of 1:5 to 2:5 and with the weight of the container material being in the range of 50 to 250 g/m$^2$.

9. A container according to claim 8, for microwave ashing of samples for ash analyses of materials, in which the cylinder measures in the range of 4 to 6 cm in diameter and in the range of 1 to 2 cm in height and weighs in the range of 0.3 to 2 g.

10. A process for manufacturing a container which is suitable for use as a container for ashable material to be ashed in an ashing furnace, which container is heat resistant during such an ashing operation, light in weight and of integral thin walled bottom and side portions which are porous to air flow through them during ashings of ashable analytical samples, which bottom and side wall portions are of non-woven microfibers which are quartz microfibers, borosilicate glass microfibers or a mixture of quartz microfibers and borosilicate glass microfibers, which non-woven microfibers are sintered together so as to be in integral walled and bottomed container form, wherein the container wall and bottom portions are resistant to a temperature of 500° C., are of a thickness in the range of 0.2 to 5 mm, are of a weight in the range of 50 to 500 g/m$^2$, are retentive of micron size particles and are of such a porosity that pressure drop across them is in the range of 0 to 10 mm of mercury at a face velocity of air in the range of 1 to 10 cm per second, which process comprises shaping a light weight, microwave transmissive and porous sheet of non-woven microfibers, which are quartz microfibers, borosilicate glass microfibers or a mixture of quartz microfibers and borosilicate glass microfibers, to integral walled and bottomed container form, wetting material of such sheet or form before heating, heating said wetted and shaped form to a sintering temperature in the range of 800° to 1,000° C. for 1 to 20 minutes, and cooling it to room temperature in room temperature air.

11. A process according to claim 13 wherein the light weight, microwave transmissive and porous sheet of non-woven microfibers is of quartz microfibers containing 0 to 10% of borosilicate glass microfibers and said sheet is wet with water before being shaped to container form.

12. A process according to claim 10 wherein the porous sheet is of a thickness in the range of 1 to 4 mm, is of such porosity that pressure drop across it is in the range of 0 to 6 mm of mercury at a face velocity of air of about 1 cm per second, is heat resistant, with embrittlement, to high temperatures, up to 1,000° C., is retentive of over 99% of micron size particles and is transparent to microwave radiation.

13. A process according to claim 12 wherein the container resulting is of substantially flat cylindrical form, with the height : diameter ratio thereof being in the range of 1:5 to 2:5 and with the weight of the container material being in the range of 50 to 500 g/m$^2$.

14. A process according to claim 13 wherein the container resulting is useful for microwave ashing of samples for ash analyses of materials, and in which the container resulting is a cylinder measuring in the range of 4 to 6 cm in diameter and in the range of 1 to 2 cm in height, and weighs in the range of 0.3 to 2 g.

15. A process of manufacturing a container for a material which is to be heated therein, which comprises shaping a light weight microwave transmissive, heat resistant and porous sheet of quartz fibers, borosilicate glass fibers or a mixture of quartz fibers and borosilicate glass fibers, to container form, including integral bottom and side wall portions, heating said sheet in said form to a sintering temperature and cooling said container form, so that a form retaining integral porous container results, through the bottom and side wall partions of which air can pass and in which container micron size particles are retained.

16. A process according to claim 15 wherein the heating is to a sintering temperature of at least 400° C.

17. A process according to claim 16 wherein the heating is for 1 to 20 minutes and after completion of heating the container is cooled to room temperature in room temperature air.

18. A process according to claim 17 wherein the porous sheet is of quartz microfibers, is wet with water before heating and heating is to a sintering temperature in the range of 800° to 1,000° C.

19. A process according to claim 18 wherein the porous sheet is of quartz microfibers contains 0 to 10% of borosilicate glass microfibers.

* * * * *